US 8,214,082 B2

(12) United States Patent
Tsai et al.

(10) Patent No.: US 8,214,082 B2
(45) Date of Patent: Jul. 3, 2012

(54) NURSING SYSTEM

(75) Inventors: Chi-Yi Tsai, Kaohsiung (TW);
Fu-Sheng Huang, Jhongli (TW);
Chen-Yang Lin, Sijhih (TW);
Zhi-Sheng Lin, Sinjhuang (TW);
Chun-Wei Chen, Shalu Township (TW);
Kai-Tai Song, Hsinchu (TW)

(73) Assignee: National Chiao Tung University, Hsinchu, Taiwan (TW)

( * ) Notice: Subject to any disclaimer, the term of this patent is extended or adjusted under 35 U.S.C. 154(b) by 919 days.

(21) Appl. No.: 12/062,843

(22) Filed: Apr. 4, 2008

(65) Prior Publication Data
US 2009/0198374 A1    Aug. 6, 2009

(30) Foreign Application Priority Data

Jan. 31, 2008  (TW) .............................. 97103671 A

(51) Int. Cl.
*G05B 19/04* (2006.01)
*A61B 5/00* (2006.01)
(52) U.S. Cl. ......................................... 700/253; 600/300
(58) Field of Classification Search .................. 700/244, 700/245, 255, 259, 257, 56, 59, 62, 64, 65, 700/90, 250, 253, 258; 382/103; 705/2; 600/300, 382, 415, 424; 340/539.22
See application file for complete search history.

(56) References Cited

U.S. PATENT DOCUMENTS

| | | | | |
|---|---|---|---|---|
| 7,228,203 | B2 * | 6/2007 | Koselka et al. | 700/245 |
| 2005/0245839 | A1 * | 11/2005 | Stivoric et al. | 600/549 |
| 2008/0001735 | A1 * | 1/2008 | Tran | 340/539.22 |
| 2010/0316253 | A1 * | 12/2010 | Yang et al. | 382/103 |

OTHER PUBLICATIONS

"Development of a Robot to Help Elderly People at Home", Kai-Tai Song et al., Proceedings of 2007 CACS International Automatic Control Conference National Chung Hsing University, Taichung, Taiwan, Nov. 9-11, 2007, 7 pages.*

* cited by examiner

*Primary Examiner* — Mary Cheung
(74) *Attorney, Agent, or Firm* — Bui Garcia-Zamor; Hung H. Bui, Esq.

(57) ABSTRACT

A nursing system of the present invention can position where a person to be nursed through a sensor network widely deployed in an environment, instantaneously detect if the person to be nursed has an accident, and forward a message to inform a relative or medical staff. An autonomous robot will actively move beside the person to be nursed and transmit real-time images to a remote computer or PDA so that the relative or medical staff can swiftly ascertain the situation of the person to be nursed and the person to be nursed in case of emergency can be rescued as soon as possible.

20 Claims, 5 Drawing Sheets

NURSING SYSTEM

CROSS-REFERENCE TO RELATED APPLICATION

This application claims all benefits accruing under 35 U.S.C. §119 from Taiwanese Patent Application No. 097103671, filed on Jan. 31, 2008 in the Intellectual Property Office Ministry of Economic Affairs, Republic of China, the disclosure of which is incorporated by reference herein.

FIELD OF THE INVENTION

The present invention relates to a nursing system, and more particularly to an autonomous system having nursing capability.

BACKGROUND OF THE INVENTION

There is an autonomous personal service robot disclosed in U.S. Pat. No. 7,228,203 for mainly monitoring the condition of surrounding environment, such as smoke, heat and $CO_2$ content, and addressing the functions of medicine supply, blood pressure measurement, and connection with refrigerator and stereo system. However, the robot is weak in monitoring a person to be nursed, making it infeasible to get hold of timely physical complaint of the person to be nursed.

Besides, there is also a medical tele-robotic system disclosed in U.S. Pat. No. 7,218,992, in which the system contains a robotic arm, and communication interfaces, e.g. a monitor, a webcam, etc., enabling to remotely remind a person to be nursed to take medicine. It mainly lies in that the robotic system has an arm capable of grabbing an object for a remote person to be nursed. Although the robotic system provides an arm to grab, it still mainly counts on remote control instead of self-positioning and navigation.

Moreover, there are relevant literatures as follows:
[1] B. Graf, M. Hans, J. Kubacki and R. D. Schraft "Robotic home assistant Care-O-Robot," in Proc. of the second joint EABS/BMES conference, Houston, USA, 2002, pp. 2343-2344; and
[2] Z. Dehuai, X. Cunxi and L. Xuemei "Design and implementation of internet based health care robot system," in Proc. of the 2005 IEEE Engineering in Medicine and Biology 27th Annual Conference, Shanghai, China, 2005, pp. 577-580.

With emphasis on the features of autonomous patrol, escort or care of a person to be nursed, the robots in the literatures [1] and [2] lacks of emergency processing feature. If a person to be nursed incurs an accident and there's no way that the robots are aware of that, no relevant countermeasure can be taken at all.

SUMMARY OF THE INVENTION

To solve the aforementioned problem, the object of the present invention is to provide a nursing system for helping a person to be nursed (e.g. the aged, child or patient) so as to immediately inform relevant person (e.g. relative or nursing staff) in case of an emergency (e.g. inadvertent fall) happening to the person to be nursed.

The present invention provides a nursing system, including a nursing apparatus having an on-board computer for controlling the nursing apparatus; a camera and a head motion mechanism in which the camera mounted on the head motion mechanism and controlled by the computer rotates in multi-angular directions for capturing image signals and forwarding them to the computer; a moving platform controlled by the computer for moving the nursing apparatus; a ZigBee module for receiving a signal from a wireless sensor network (WSN) and transmitting it to the computer; a laser scanner for detecting any blockade around the nursing system and transmitting data to the computer; an input/output (I/O) device connected with the computer for a user to communicate with the nursing apparatus; a body pose recognition system carried on the person to be nursed for determining if the person to be nursed falls down in accordance with a body pose determined by a triaxial accelerometer and generating a determination result signal; and the WSN receiving the determination result signal from the body pose recognition module and transferring it to the nursing apparatus.

The present invention combines the nursing system, wireless sensor nodes deployed in an environment and the pose recognition module carried on a person to be nursed to make the nursing system instantaneously detect the situation of the person to be nursed and actively navigate to approach the person to be nursed so as to keep track of the face thereof, transmit real-time images to a relative or nursing staff, and enable the person to be nursed to receive more timely rescue.

DETAILED DESCRIPTION OF THE PREFERRED EMBODIMENT

Hardware structure—A nursing system of a preferred embodiment is built under an environment of a ZigBee WSN and includes a robot of living aid (RoLA) 100, a ZigBee WSN 200 and a body pose recognition module 300.

The composition and operation details of each mechanism in the preferred embodiment are thoroughly described as follows.

Figure 1:
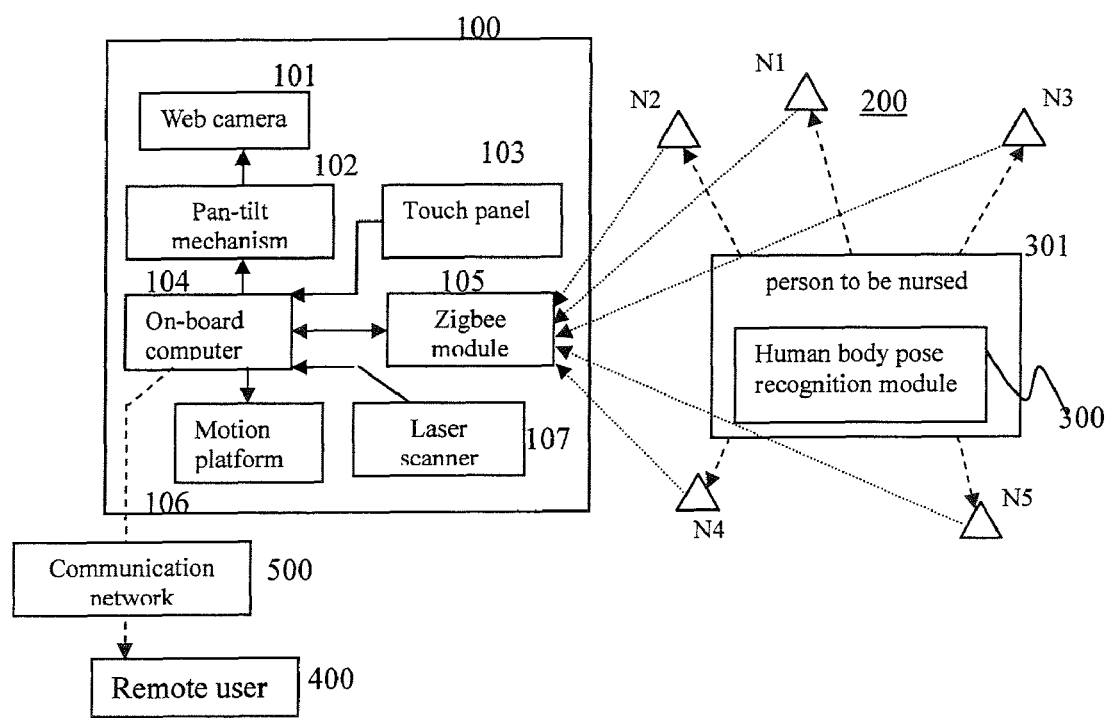
FIG. 1 is a schematic view showing blocks constituting the RoLA system.

Firstly, as shown in the left side of FIG. 1, the RoLA 100 is constructed on the moving platform 106 with dual independently driving wheels and controls two motor speeds of the moving mechanism 106 to make the robot move on a plane. An additional passive free caster is located behind the moving platform 106 to address a tri-wheel design that enables the RoLA 100 to smoothly and stably move in an indoor environment.

A motor-driven pan-tilt mechanism 102 located at the head of the RoLA 100 has a webcam 101 thereon and can control the webcam 101 to tilt up and down and pan left to right so as to realize the function face-tracking control. There is a laser scanner 107 disposed at a front bottom end for detecting any blockade ahead so as to dodge. An on-board computer 104 of the robot adopts an industrial single board computer featuring advantages of being small in size and low in power consumption, making it ideal for the application of moving robot. A ZigBee module 105 on the RoLA 100 serves as a receiving end of the ZigBee WSN 200 in an environment. A touch screen 103 is provided to the front side of the RoLA 100 to easily interact with people.

Next, as to the aspect of the body pose recognition module 300, the embodiment uses the ZigBee WSN 200 as a transmission medium, thereby providing body pose information of a person to be nursed 301. The body pose recognition module contains a ZigBee RF chip, a microcontroller and a triaxial accelerometer. Acceleration of human body can be measured through the triaxial accelerometer of the module to further determine the body pose of the person to be nursed 301.

As to the aspect of the ZigBee WSN 200, it is composed of multiple ZigBee sensor nodes N1~N5 in the environment and forms a sensor network structure together with the body pose recognition module 300 carried by the person to be nursed 301. As shown in the right side of FIG. 1, in the Zig Bee WSN 200 information of the body pose recognition module 300 can be transmitted to the ZigBee module 105 of the RoLA 100 by relaying through nodes N1~N5 for analysis of each data.

Detection method—The body pose recognition module 300 is disposed on a waist portion of a body, and the acceleration value of this position represents a state of the center of gravity of the entire body. A right direction, top direction and rear direction of the body are defined to be X axis, Y axis and Z axis respectively. The triaxial accelerometer can measure a dynamic acceleration of the body and the acceleration of gravity arising from the gravitational force, however, the pose while a person falls down is relevant to the dynamic acceleration generated by human body only. Therefore, an acceleration signal shall be preprocessed so as to separate the dynamic acceleration from the static acceleration and detect a stumbling pose with the dynamic acceleration signal.

Figure 2:
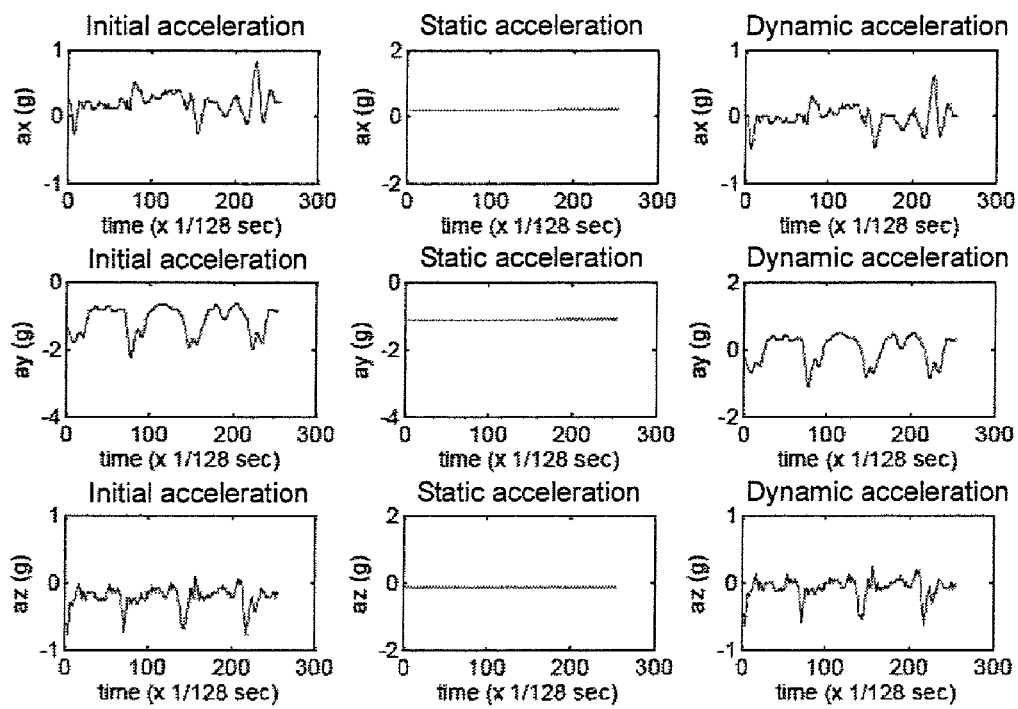
FIG. 2 is diagrams showing results of dynamic acceleration and static acceleration after a wavelet transform.

Signal preprocessing—The exercise frequency of a human body is usually less than 20 Hz. In the embodiment, an adopted sampling frequency is 128 Hz. After collecting data in every two seconds, the embodiment processes a pose algorithm, i.e. a processing for every 256 data. A wavelet transform is used to calculate the static acceleration. As there are only 256 data acquired, 8-layer Haar wavelet transform can be performed. Only the layer with the lowest frequency, which represents a wavelet coefficient in a range of 0~0.25 Hz, is taken here. The coefficient is recovered to that in the time domain, which represents a DC component within the two seconds. The dynamic acceleration is obtained by subtracting the static acceleration signal from the original acceleration signal. FIG. 2 illustrates the results of dynamic and static accelerations obtained after the wavelet transform.

Figure 3:
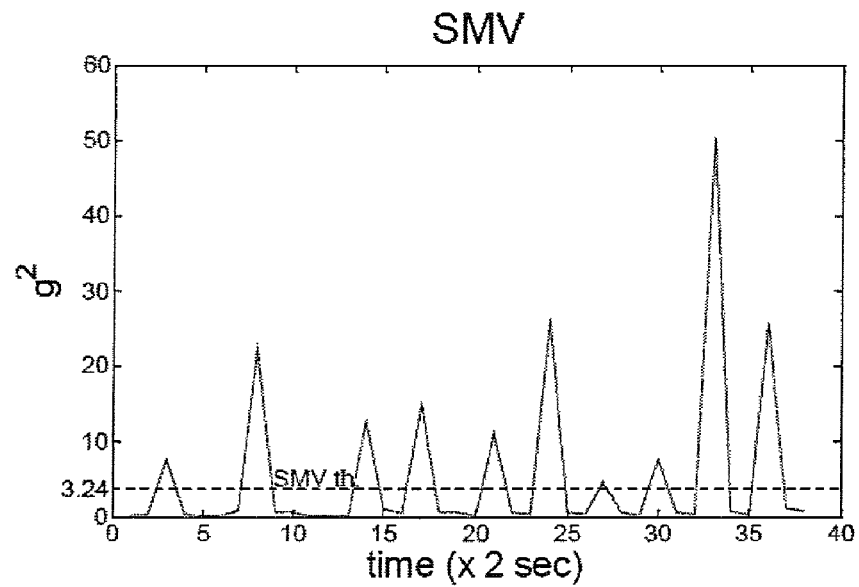
FIG. 3 is a waveform diagram showing the signal magnitude vectors when a testee is stumbling during walking.

Stumbling determination—In view of the generated dynamic acceleration far greater than those arising from other movements of body, if the dynamic acceleration upon stumbling is quantified by a signal magnitude vector (SMV) in accordance with actually measured data, a stumbling pose very likely happens when SMV>3.24.

$$SMV = a_{x\_dynamic}^2 + a_{y\_dynamic}^2 + a_{z\_dynamic}^2 \qquad (1)$$

where $a_x$, $a_y$, $a_z$ in the above equation are the dynamic acceleration values (unit: g) in the X, Y, Z direction respectively. Based on the actually measured data, FIG. 3 is a waveform diagram recording states while a testee stumbles 10 times during walking, in which 10 conspicuous pulses occur when stumbling. As a result, the condition, SMV>3.24, is used determine if a stumbling condition happens.

Indoor positioning design—In the embodiment, the WSN 200 deployed with the ZigBee sensor nodes N1~N5 is used to design a set of indoor positioning system which can locate any object or personnel having a ZigBee module 105 in the deployed environment. The nodes N1~N5 in the environment are used to receive the received signal strength (RSS) sent by the ZigBee module 105 on a target object to provide an actual position information of the object. While establishing the positioning system, two steps are classified: (1) creating a position database, and (2) estimating position, as described below.

(1) creating a position database—First create enough reference points in the working environment and collect a certain quantity of signal strength on those reference points to generate the position database with those collected samples; before using RSS as spatial characteristic, usually first create the position database; record the average value of the RSS samples collected on each reference point with respect to each ZigBee sensor node so that each datum recorded in the position database is expressed by $(x_i, y_i, ss^1i, ss^2i, \ldots, ss^ni)$ where $x_i$ and $y_i$ represent the position of the ith reference point in the environment, $ss^1i, ss^2i, \ldots, ss^ni$ represent the average signal strength of each ZigBee sensor node received at $(x_i, y_i,)$, in which n is the number of the ZigBee sensor nodes deployed in the environment; and distinguish the position of each reference point with these signal strengths.

(2) estimating position—use the signal strength on an unknown position in the working environment received through the ZigBee module 105 equipped on the RoLA 100 to compare with records in the position database so as to estimate the actual position of the RoLA 100 in the environment. The determination algorithm used in the embodiment is called Nearest Neighbor Algorithm (NNA) and Nearest Neighbor Average Algorithm (NNAA). The NNA directly compares the obtained RSS value with data in the position database to choose a nearest position as the position where the current user is located. Such method employs a database created by the ZigBee nodes deployed in the environment to determine the positioning accuracy. Consequently, the deployment of the ZigBee nodes N1~N5 needs to be carefully chosen.

Navigation Behavior of Robot

Figure 4:
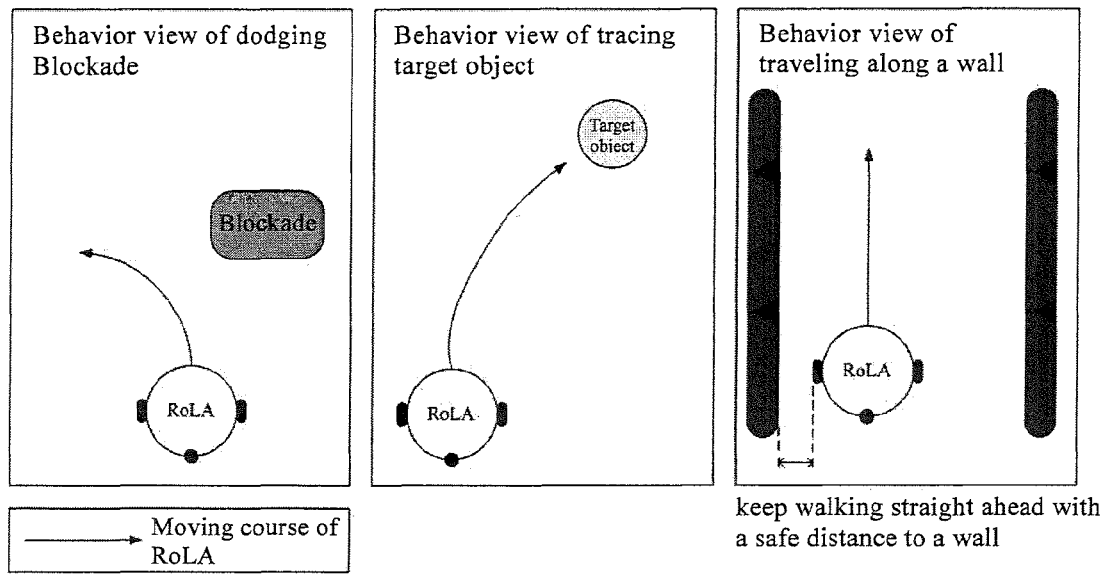
FIG. 4 is a schematic view dividing navigation tasks into three types of behaviors.

Design of navigation behavior—The navigation design of RoLA 100 adopts a behavior-based structure which classifies navigation tasks into three types of behaviors to process, namely dodging blockade, tracing target and walking along a wall, as shown in FIG. 4.

The three types of behaviors target at making the RoLA dodge a blockade ahead, adjusting the moving course of RoLA to make it approach a target object, and making the RoLA to move along the boundary of the environment and maintain a fixed distance away from a closer side of the boundary. The three behavior designs are completed by using three respective fuzzy behavior controllers capable of effectively reducing computation overhead and accelerating processing speed. The sensed information of the laser scanner 101, the position of the target object and the robot location transmitted by the odometer established by an encoder and the ZigBee positioning system are inputted to the fuzzy behavior controllers in the on-board computer 104, and the fuzzy behavior controllers will output the corrected values of the rotation speed of the two wheels to the moving platform 106. Therefore, the RoLA 100 will move forward with an initial linear speed first. If the three fuzzy behavior controllers output no signal at all, the RoLA 100 will continue moving forward without changing the course. Otherwise, if the three fuzzy behavior controllers output signals, the corrected values of the two wheels of the moving platform 106 are calculated by a behavior fusion method to achieve the navigation behavior of the RoLA 100.

Behavior fusion—Speaking of the RoLA 100, how to select an adequate behavior in response to environmental change is an essential subject to be solved in navigation design. The positional estimation of the odometer, the environmental information of the laser scanner 101 and the orientation of the target object are inputted to the RoLA 100, and the final rotation speeds of the two wheels of the moving platform 106 are calculated by the behavior fusion method to achieve the navigation behavior function.

Human face detection and tracking system—To know the condition of a person to be nursed 301 at home, the embodiment discloses a human face detection and tracking system using the camera 101 disposed on the RoLA 100 to capture image and detect the position of a human face on a screen, and possesses a pan-tilt mechanism 102 capable of moving up and down as well as left and right, so as to stably move the camera 101 and keep track of still and moving faces of the person to be nursed 301. Therefore, the RoLA 100 can infallibly get hold of the situation of the person to be nursed 301. In the end, the images are transmitted through wireless networks, allowing the remote user 400 (a relative or medical staff) to also catch sight of the situation of the person to be nursed 301 (please refer to FIG. 1).

Face detection algorithm—To smoothly keep track of a human face, the face position needs to be correctly detected first in the image. The embodiment employs a real-time face detection method based on skin color detection and utilizes an adaptive skin color search method to achieve stable tracking of human face.

Figure 5:
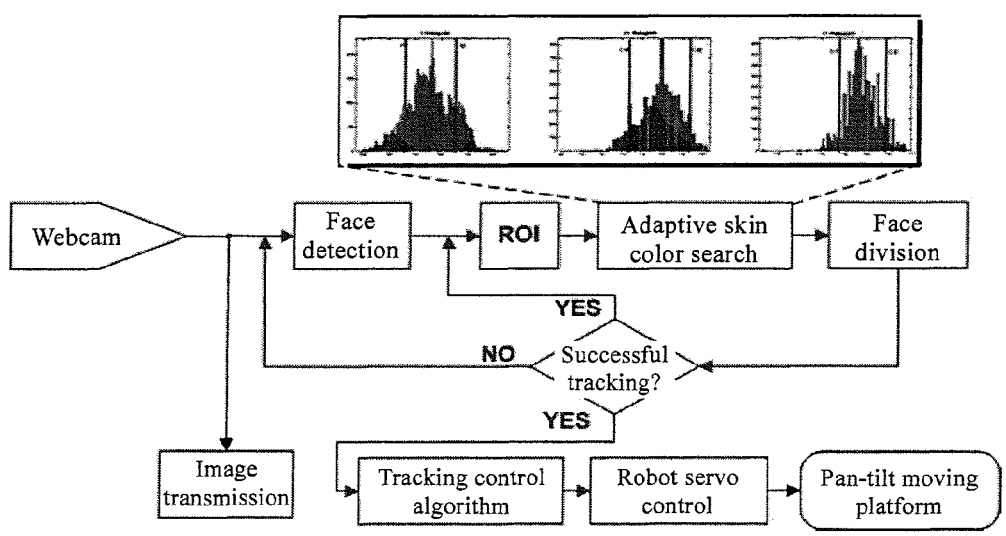
FIG. 5 is a flow diagram showing the algorithm for detecting and tracing a human face.

FIG. 5 is a flow chart diagram illustrating the human face detection and tracking algorithm, which includes steps of using a webcam 101 to capture image, starting the face detection algorithm in addition to transmitting real-time images, using skin color detection to ascertain a possible face position, and defining an adaptive skin color window in the region of interest (ROI) which is a region for compiling statistics of threshold for skin color distribution. In the present invention, YCrCb colors are used. Color histograms are shown on the top side of FIG. 5. First calculate an average brightness inside the window and obtain the top and bottom thresholds of a 3D YCrCb color distribution in accordance with the average brightness, and then define top and bottom margins for screening to just leave most intermediate color ranges of typical skin color for the time being serving as the skin color division basis for the next time.

As a result of real-time update of color ranges for skin color division, the face detection system possesses the characteristics against variation of light source. Under the condition when light source is brighter or darker, the system can still divide the region of face color to detect the correct position of the face. Such adaptive skin color search method can more stably keep track of the color blocks of human face, enabling to make face detection and tracking even more stable. After successfully recognizing the positions of human face blocks, the tracking control rule can then be used. The motor of the pan-tilt mechanism 102 is controlled through a motion controller of the RoLA 100 to rotate the camera 101 and make the camera 101 constantly face to the position of human face.

Figure 6:
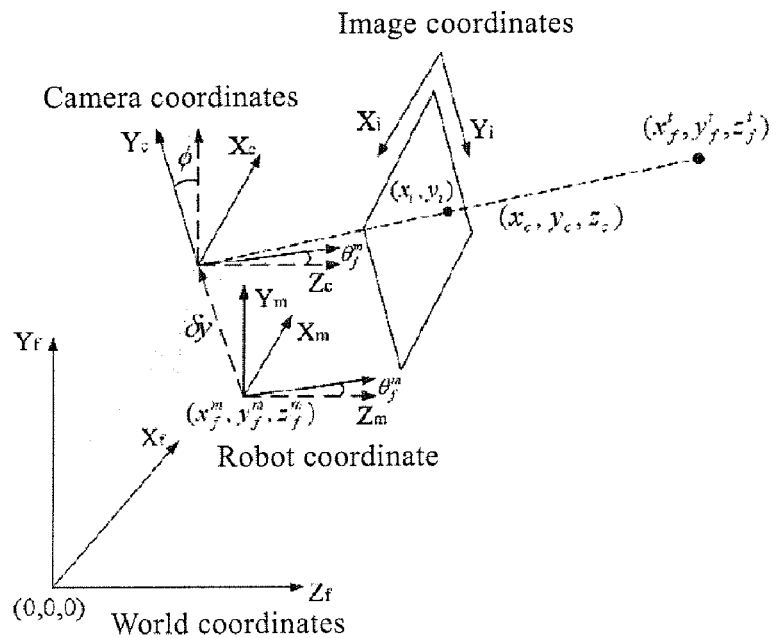
FIG. 6 is a relationship diagram in association with world coordinates of robot, camera coordinates and an image coordinate plane.

Face tracking control method—FIG. 6 is a relationship diagram among world coordinates of robot, camera coordinates and an image coordinate plane. To design a controller to control the movement of the camera 101, first drive a new model with respect to the moving control of robot on the image plane according to FIG. 6, and build the dynamic relationship between robot and target object. For sake of controlling this system, the system model is converted to drive a dynamic error-state model. Consequently, the original vision tracking control problem is converted into a problem of stability. If all errors can be converged to zero, the vision tracking control problem can thus be solved so that the orientation of the camera can be stably controlled to maintain the target object at the center of the image plane.

The present invention employs a tracking control design such that the system possesses robust characteristic against the parametric uncertainties. The controller is realized on the RoLA 100 to achieve the function of stably moving and keeping track of the face of a person. Based on the aforementioned face detection and tracking method, the face detection and tracking system can keep track of the face position of a person and maintain the face position at the central portion of the screen, thereby keeping track of the face on a real-time basis and achieving expected functionality.

Short message notice and video transmission—If the person to be nursed 301 incurs an emergency, the RoLA 100 shall be able to inform a relative or medical staff within a shortest period of time. The best way is to send a short message with a mobile phone and use a wireless network (WiFi or 3G network) to transmit video frames to the mobile phone of a family member. No matter where the family member is, the message can be received instantaneously as long as the signal can reach the mobile phone. When the person to be nursed falls down, the robot will immediately detect the occurrence of the abnormal condition and send a short message to the family of the person to be nursed 301 via a communication network, enabling the family to be aware of the situation and perform a contingency processing and making the person to be nursed 301 accessible by rescue assistance.

Moreover, to make remote family member more clearly understand the situation of the person to be nursed 301, the present invention further provides a transmission device that can transmit images captured by a camera to a remote end. As long as a networking environment (e.g. WiFi or 3G) is available, a remote family member can use a mobile phone, personal computer, PDA or smart phone to monitor the condition at home on a real-time basis. Furthermore, together with the above-mentioned face tracking function, the images of the person to be nursed can be instantly monitored to promptly get hold of the condition of the health of the person to be nursed 301.

Figure 7:
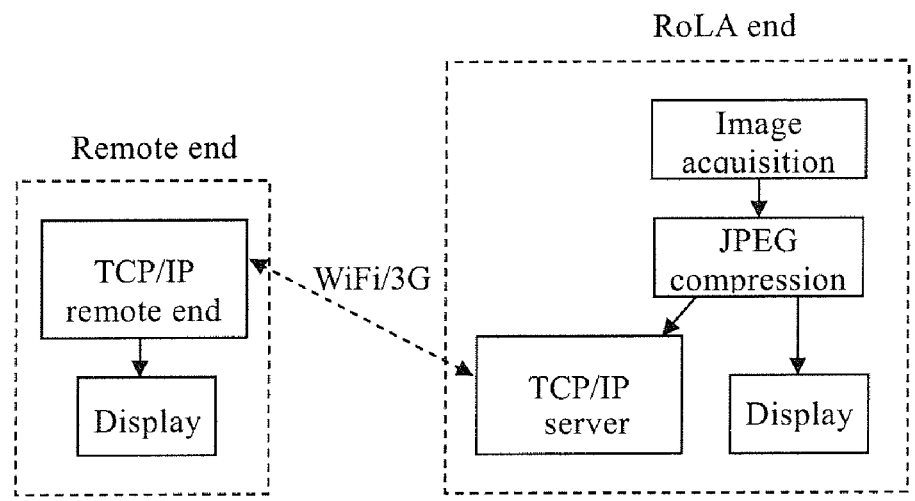
FIG. 7 is a design diagram showing an image transmission structure.

FIG. 7 shows a structural design of image transmission, in which the transmitting end acquires images through the USB webcam 101 and employs JPEG compression to transmit the images out through a TCP socket port via a WiFi/3G network, and the receiving end also employs a TCP socket port to receive data from the network and displays the JPEG pictures on the screen.

Figure 8:
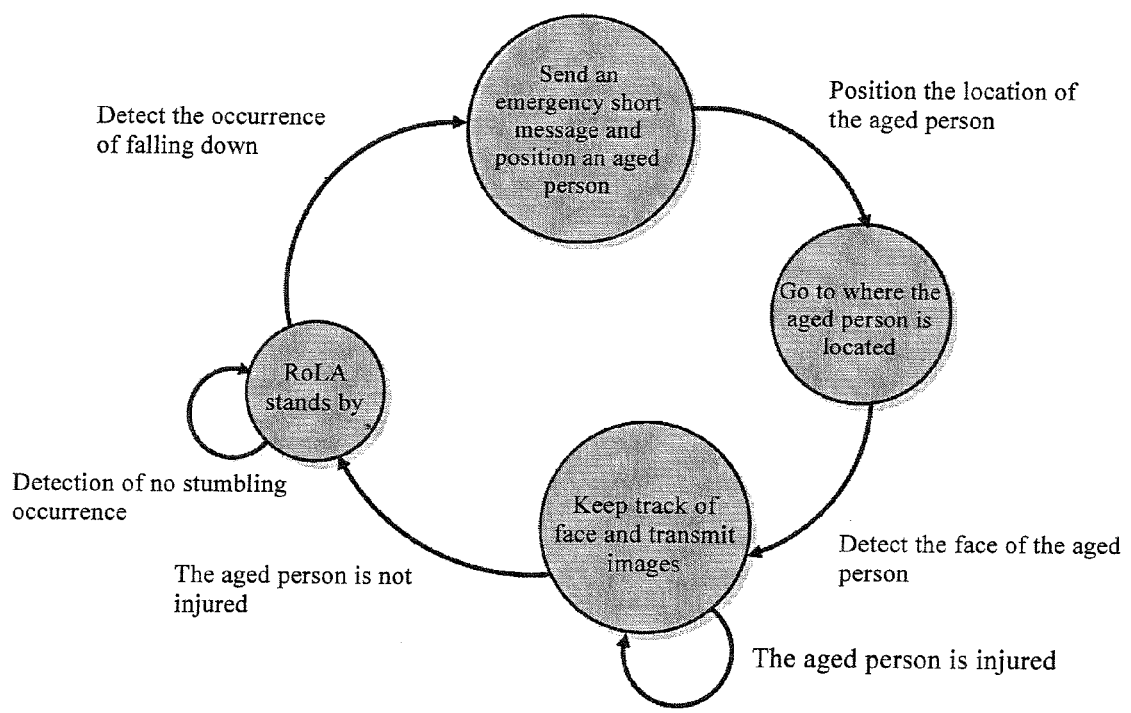
FIG. 8 is a state flow diagram showing the nursing system.

FIG. 8 is a state flow diagram showing operation of the nursing system. The figure explains an application scenario of the nursing system. When the body pose recognition module 300 carried on the person to be nursed 301 detects that the person to be nursed 301 falls down, a signal will be transmitted to the on-board computer 104 of the RoLA 100 via the ZigBee WSN 200 to inform of the occurrence of emergency. Upon knowing that the person to be nursed 301 falls down, the on-board computer 104 will first transmit a short message to the mobile phone of the family immediately and then determine where the person to be nursed 301 is located through the positioning system constructed by the ZigBee WSN 200. The RoLA 100 can actively move beside the person to be nursed 301 by virtue of the self-moving behavior. At the moment, the webcam 101 disposed on top of the RoLA 100 automatically follows the face of the person to be nursed and the images are transmitted out via a WiFi/3G network. A remote medical staff can watch real-time images of the person to be nursed 301 through a PDA or smart phone to get hold of the latest and most correct situation and render appropriate assistance to the person to be nursed 301.

In sum, despite a robotic application depicted in the embodiment, the present invention is not limited to this only. The structure of the present invention can be also suitable for other applications such as electronic pets. Although the description of the present invention involves in indoor applications, it can be adapted to both indoor and outdoor applications, e.g. outdoor courtyard of a house, as long as it is within the network coverage.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A nursing system, comprising:
   a nursing apparatus comprising an on-board computer for controlling the nursing system; a head motion mechanism controlled by the on-board computer; a camera disposed on and driven by the head motion mechanism to rotate in multi-angle directions for capturing and forwarding images to the on-board computer; a moving platform controlled by the on-board computer to move the nursing apparatus; a ZigBee module for receiving signals from a wireless sensor network and transmitting the signals to the on-board computer; a laser scanner for detecting if there is any blockade around the nursing apparatus and transmitting information to the on-board computer; and an I/O device connected with the on-board computer for a user to communicate with the nursing apparatus; and
   a body pose recognition module attached to a person to be nursed for detecting a body pose of the person by a triaxial accelerometer so as to determine if there is an emergency and to generate a determination result signal;
   wherein:
   the wireless sensor network is disposed as a positioning system for determining a position of the person to be nursed, receiving the determination result signal from the body pose recognition module and transferring the determination result signal to the nursing apparatus, via the ZigBee module,
   the positions of the person to be nursed and the nursing apparatus are located according to a signal strength sent through the wireless sensor network,
   the on-board computer is provided with a navigation behavior control function for controlling the moving platform according to detected information of the laser scanner, the positions of the person to be nursed and the nursing apparatus so as to enable the nursing apparatus to perform a plurality of specific moving behaviors, and
   the on-board computer models the dynamic relationship between the nursing apparatus and the person to be nursed as a linear-time-varying system (LTV), and converts the coordinates of the nursing apparatus and the camera to derive a dynamic error-state model with reference to an image plane of the camera so that the image of the person to be nursed is maintained at the center of the image plane of the camera.

2. The nursing system of claim 1, further comprising a remote receiver for receiving signals issued by the nursing apparatus, via an external network.

3. The nursing system of claim 2, wherein the external network is a WiFi/3G network system.

4. The nursing system of claim 2, wherein the remote receiver comprises one selected from a group consisting of a mobile phone, a personal computer, a PDA and a smart phone.

5. The nursing system of claim 2, wherein the on-board computer is further provided with an emergency message transmission function for transmitting an emergency message to the remote receiver equipped on a medical staff or a family member, via the external network.

6. The nursing system of claim 5, wherein the nursing person is one of a relative or a medical staff.

7. The nursing system of claim 1, wherein the on-board computer is further provided with a human face tracing and detecting function for using the camera to capture the image and detect a position of a face of the person to be nursed in the image and controlling the head motion mechanism to stably move the camera so as to keep track of the face of the person to be nursed.

8. The nursing system of claim 1, wherein the specific moving behaviors comprise:
   a blockade-dodging behavior for making the nursing apparatus dodge a blockade ahead;
   a target-tracing behavior for adjusting a forward-moving direction of the nursing apparatus so that the nursing apparatus moves toward the person to be nursed; and
   a boundary-moving behavior for making the nursing apparatus move forward along a boundary of an environment by keeping a fixed distance away from a closer side of the boundary.

9. The nursing system of claim 1, wherein the body pose recognition module is mounted to a waist portion of the person to be nursed and utilizes a dynamic acceleration value at the waist portion to represent a state of a center of gravity of the person to be nursed.

10. The nursing system of claim 9, wherein the body pose recognition module measures the dynamic acceleration value of the person to be nursed and acquires the dynamic acceleration value with a triaxial accelerometer to determine a body pose of the person to be nursed.

11. The nursing system of claim 10, wherein an X-axis, a Y-axis and a Z-axis are defined in a right direction, a top direction and a rear direction of a body of the person to be nursed respectively.

12. The nursing system of claim 1, wherein the camera further comprises:
   an image compression function for processing received images; and
   a video transmission function for transmitting the received images from the on-board computer to the remote receiver, via the external network.

13. The nursing system of claim 1, wherein the person to be nursed is one selected from a group consisting of an aged person, a child or a patient.

14. A nursing system, comprising:
   a nursing apparatus comprising an on-board computer for controlling the nursing system; a camera disposed on a head motion mechanism to rotate in multi-angle directions for capturing and forwarding an image; a ZigBee module; a laser scanner disposed to detect if there is any blockade around the nursing apparatus;

a body pose recognition module attached to a person to be nursed for detecting a body pose of the person so as to determine if there is an emergency, and for communicating with the Zigbee module of the nursing apparatus, via a wireless sensor network; and a remote receiver for receiving signals issued by the nursing apparatus, via an external network, wherein the body pose recognition module is mounted to a waist portion of the person to be nursed and utilizes a dynamic acceleration value at the waist portion to represent a state of a center of gravity of the person to be nursed, and wherein the on-board computer models the dynamic relationship between the nursing apparatus and the person to be nursed as a linear-time-varying system (LTV), and converts the coordinates of the nursing apparatus and the camera to derive a dynamic error-state model with reference to an image plane of the camera so that the image of the person to be nursed is maintained at the center of the image plane of the camera.

15. The nursing system of claim 14, wherein the remote receiver comprises one selected from a group consisting of a mobile phone, a personal computer, a PDA and a smart phone, and wherein the external network is a WiFi/3G network system.

16. The nursing system of claim 14, wherein the on-board computer is installed in the nursing apparatus to capture the image and detect a position of a face of the person to be nursed in the image, and to control the head motion mechanism to move the camera so as to keep track of the face of the person to be nursed.

17. The nursing system of claim 14, wherein the body pose recognition module measures the dynamic acceleration value of the person to be nursed and acquires the dynamic acceleration value with a triaxial accelerometer to determine a body pose of the person to be nursed.

18. The nursing system of claim 16, wherein the on-board computer installed in the nursing apparatus is further configured to transmit an emergency message to the remote receiver equipped on a medical staff or a family member, via the external network.

19. A nursing system, comprising:

a nursing apparatus comprising a camera arranged to rotate in multi-angle directions and capture images; a moving platform; a ZigBee module arranged to communicate, via a wireless sensor network; a laser scanner arranged to detect if there is any blockade around the nursing apparatus; and an on-board computer arranged to control the camera, the moving platform, the ZigBee module and the laser scanner; and a body pose recognition module attached to a person to be nursed to detect a body pose of the person so as to determine if there is an emergency, wherein the wireless sensor network is disposed as a positioning system to determine a position of the person to be nursed, wherein positions of the person to be nursed and the nursing apparatus are located according to a signal strength sent, via the wireless sensor network, wherein the on-board computer is provided with a navigation behavior control function to control the moving platform according to information from the laser scanner, the positions of the person to be nursed and the nursing apparatus so as to enable the nursing apparatus to perform a plurality of specific moving behaviors, and wherein the on-board computer models the dynamic relationship between the nursing apparatus and the person to be nursed as a linear-time-varying system (LTV), and converts the coordinates of the nursing apparatus and the camera to derive a dynamic error-state model with reference to an image plane of the camera so that the image of the person to be nursed is maintained at the center of the image plane of the camera.

20. The nursing system of claim 19, further comprising a remote receiver coupled to receive signals issued by the nursing apparatus, via an external network, wherein the remote receiver is one of a mobile phone, a personal computer, a PDA and a smart phone.

* * * * *